US 6,742,407 B2

(12) United States Patent
Silvis et al.

(10) Patent No.: US 6,742,407 B2
(45) Date of Patent: Jun. 1, 2004

(54) PARTICULATE SAMPLING PROBE AND DILUTION TUNNEL

(75) Inventors: William Martin Silvis, Ann Arbor, MI (US); Norbert Kreft, Ann Arbor, MI (US); Gerald Marek, Ann Arbor, MI (US)

(73) Assignee: AVL North America Inc., Plymouth, MI (US)

(*) Notice: Subject to any disclaimer, the term of this patent is extended or adjusted under 35 U.S.C. 154(b) by 0 days.

(21) Appl. No.: 10/254,056

(22) Filed: Sep. 24, 2002

(65) Prior Publication Data

US 2003/0033891 A1 Feb. 20, 2003

Related U.S. Application Data

(63) Continuation-in-part of application No. 09/816,844, filed on Mar. 23, 2001, now Pat. No. 6,481,299.

(51) Int. Cl.[7] ................................................. G01N 1/10
(52) U.S. Cl. .................................................. 73/864.73
(58) Field of Search ........................ 73/863.01, 863.02, 73/863.03, 863.11, 864.73, 23.31, 23.32, 23.33, 864.81

(56) References Cited

U.S. PATENT DOCUMENTS

| | | | |
|---|---|---|---|
| 4,630,464 A | | 12/1986 | Maul et al. |
| 5,090,258 A | * | 2/1992 | Yamasaki et al. ........ 73/863.03 |
| 5,161,417 A | * | 11/1992 | Strong et al. ............ 73/863.86 |
| 5,337,595 A | * | 8/1994 | Lewis ..................... 73/23.31 |
| 5,419,178 A | | 5/1995 | Decker et al. |
| 5,456,124 A | | 10/1995 | Colvin |
| 5,469,731 A | * | 11/1995 | Decker et al. ............ 73/23.31 |
| 6,148,656 A | * | 11/2000 | Breton .................... 73/23.31 |

FOREIGN PATENT DOCUMENTS

JP        2001249064        9/2001

* cited by examiner

*Primary Examiner*—Robert Raevis
(74) *Attorney, Agent, or Firm*—Carlson, Gaskey & Olds

(57) ABSTRACT

A particulate sampler is provided for use in analyzing particulate matter in exhaust gas. The sampler includes a transfer tube assembly including a probe at least partially defining a sample exhaust gas passageway. The transfer tube assembly has a first end portion with an opening for receiving exhaust gas and extends to a second end portion. A mixer receives the second end portion and includes a dilution gas passageway for carrying a dilution gas. The dilution gas passageway is in communication with the sample exhaust gas passageway for introducing the dilution gas to the exhaust gas. A tunnel is connected to the mixer and includes a gas mixing passageway extending a length for homogeneously mixing the gases together. The gas mixing passageway tapers toward the second end portion to ensure that the particulate matter mixes with the gases along the length of the gas mixing passageway without collecting in a recirculating flow area. The transfer tube includes an insulator cavity to insulate the sampler exhaust gas passageway and maintain the temperature of the exhaust gases within. Insulation may be arranged in the insulated cavity or exhaust gas may be conveyed through the insulator cavity to insulate the sample exhaust gas passageway.

8 Claims, 5 Drawing Sheets

US 6,742,407 B2

PARTICULATE SAMPLING PROBE AND DILUTION TUNNEL

RELATED APPLICATIONS

This is a Continuation-In-Part of U.S. Ser. No. 09/816,844, filed on Mar. 23, 2001, U.S. Pat. No. 6,481,299.

BACKGROUND OF THE INVENTION

This invention relates to an emissions unit for sampling exhaust gases, and more particularly, the invention relates to a particulate sampler used in analyzing the particulate matter in exhaust gases.

Particulate samplers have been used to collect particulate material found in exhaust gases and convey them to a filter or analyzer. A full flow method measures the particulates by diluting all of the exhaust gases expelled from the vehicle. However, this particulate sampling method is very costly. Alternatively, a partial flow particulate sampling method has been used in which a small probe is inserted into the tailpipe to obtain a small sample of the exhaust gases. This smaller fraction of exhaust gas is then diluted to obtain a temperature of the mixture below 125° F. (52° C.). The particulate matter in the diluted sample is measured and calculations are made to determine the total amount of particulate matter present in all of the exhaust gases expended from the vehicle. The partial flow method is much more cost effective, however, it is subject to variations due to an inability to accurately account for all of the particulate matter in the sample exhaust.

The structure of the passageways within the particulate sampler has an impact upon the accuracy of the particulate matter measurement. For example, a fraction of the particulate matter can collect on the walls of the passageways and, therefore, never reach the filter or analyzer. As a result, the particulate matter measured will be lower than the actual particulate matter in the sample exhaust gases.

The sampled exhaust gases typically are pulled through a probe to a mixer where dilution gases are introduced to the exhaust gases. From the mixer, the exhaust gases and dilution gases travel through a passageway where they are homogeneously mixed together. It is desirable to maintain the exhaust gases as close to its original exhaust gas temperature as possible to ensure accuracy. During a typical emissions test, the temperature of the exhaust gases fluctuates. Accordingly, it is desirable to accommodate these temperature fluctuations in exhaust gases during the test. That is, it is desirable that the particulate sampler collects the sample without changing the temperature of the exhaust gases until it reaches the mixing passageway. Therefore, it is desirable to provide a particulate sampler that maintains the temperature of the exhaust gases during the test while conveying all the particulate matter to the filter or analyzer.

SUMMARY OF THE INVENTION AND ADVANTAGES

The present invention provides a particulate sampler for use in analyzing particulate matter in exhaust gas. The sampler includes a transfer tube assembly including a probe at least partially defining a sample exhaust gas passageway. The transfer tube assembly has a first end portion with an opening for receiving exhaust gas and extends to a second end portion. A mixer receives the second end portion and includes a dilution gas passageway for carrying a dilution gas. The dilution gas passageway is in communication with the sample exhaust gas passageway for introducing the dilution gas to the exhaust gas. A tunnel is connected to the mixer and includes a gas mixing passageway extending a length for homogeneously mixing the gases together. The gas mixing passageway tapers toward the second end portion of the transfer tube assembly to ensure that the particulate matter mixes with the gases along the length of the gas mixing passageway without collecting in a recirculating flow area. The transfer tube includes an insulator cavity to insulate the sampler exhaust gas passageway and maintain the temperature of the exhaust gases within. Insulation may be arranged in the insulated cavity or exhaust gas may be conveyed through the insulator cavity to insulate the sample exhaust gas passageway.

Accordingly, the above invention provides a particulate sampler that conveys all the particulate matter of the exhaust gas to a filter or analyzer due to greatly minimized temperature losses.

BRIEF DESCRIPTION OF THE DRAWINGS

Other advantages of the present invention can be understood by reference to the following detailed description when considered in connection with the accompanying drawings wherein.

DETAILED DESCRIPTION OF THE PREFERRED EMBODIMENTS

Figure 1:
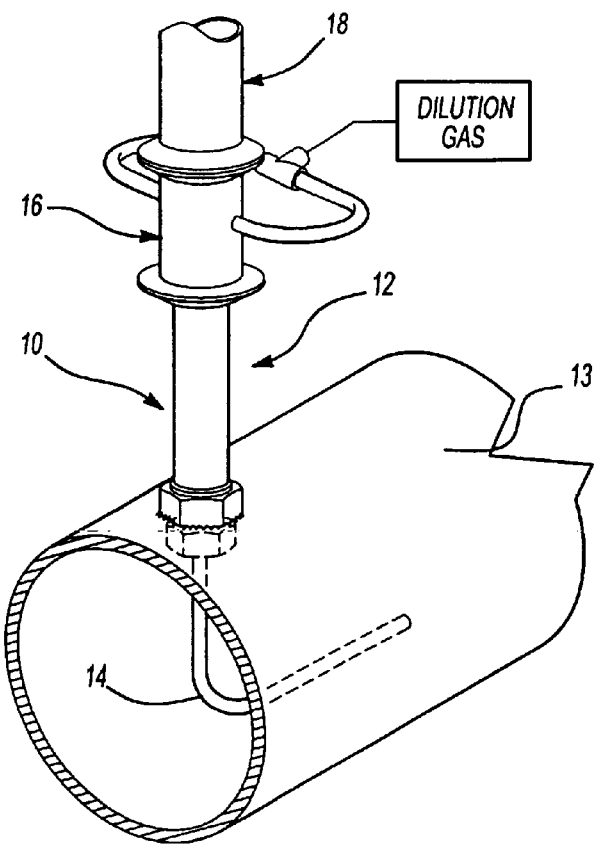
FIG. 1 is a perspective view of the probe, transfer tube and mixer of a particulate sampler.

A particulate sampler 10 preferably includes multiple components that are removably secured to one another. The components are typically constructed from stainless steel, which withstands the harsh environment of the vehicle exhaust gases. The sampler 10 includes a transfer tube assembly 12 having a probe 14. The probe 14 typically includes a curved or straight end portion that is arranged transversely in a tailpipe 13. The probe 14 collects a small exhaust gas sample that contains particulate matter. The probe 14 conveys the exhaust gas sample to a mixer 16 where a dilution gas is introduced to the exhaust gases. The dilution and exhaust gases are conveyed through a tunnel 18 where they are homogeneously mixed together. A filter holder may be connected to an end of the tunnel 18 for collecting the particulate matter on a filter or other similar device. Alternatively, an analyzer may be connected to the end of the tunnel 18 for analysis of the exhaust gas sample.

Figure 2:
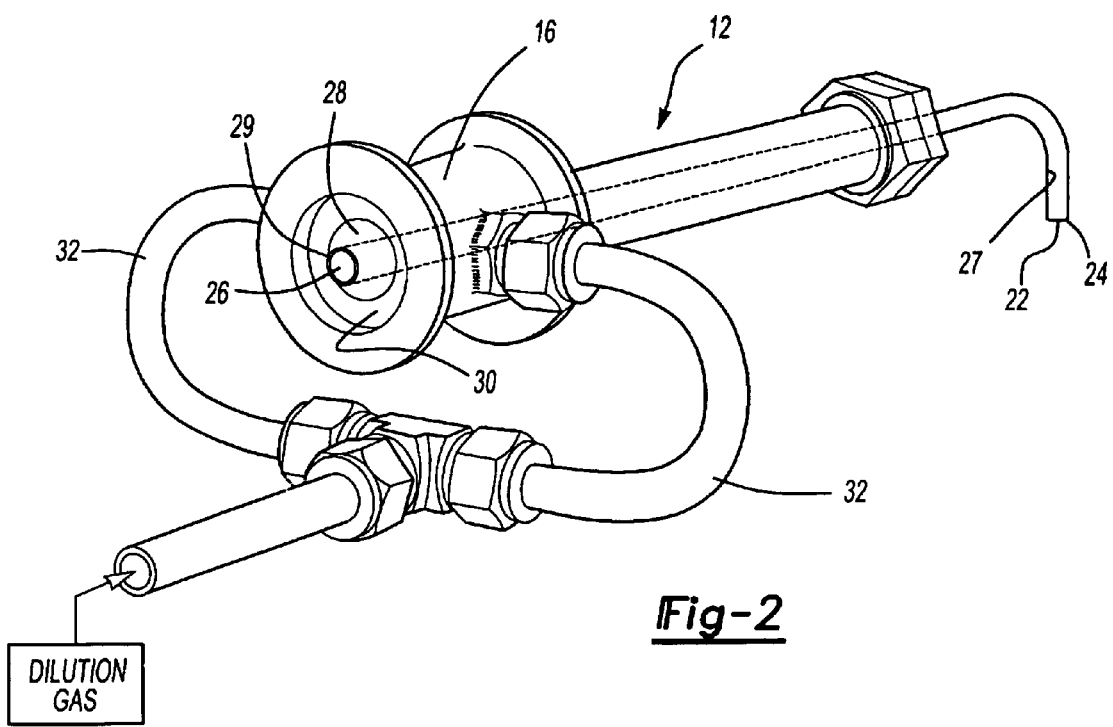
FIG. 2 is a perspective view of a mixer and transfer tube assembly.

Referring to FIG. 2, the probe 14 includes a first end portion 22 having an opening 24 for receiving the exhaust gas. The probe extends to a second end portion 26, which is adjacent to the tunnel 18 when the transfer tube assembly 12 and tunnel 18 are secured to one another. The probe 14 at least partially defines a sample exhaust gas passageway 27. The mixer includes a dilution gas chamber 30 arranged concentrically around the second end portion 26 and includes one or more feed tubes 32 defining dilution gas passageways in fluid communication therewith for conveying the dilution gas to the dilution gas chamber 30. The feed tubes 32 are arranged between the first 22 and second 26 end portions. An end section 28 is preferably secured to the second end portion of the outer tube 34. The dilution and sample exhaust gases flow parallel to and in the same direction as one another.

In the prior art, the probe was constructed from a long, thick tube having a wall thickness of approximately 0.040 inch; this tube was insulated and heated by heater tape to a temperature of 150 to 180° C. The probe of the present invention utilizes a wall thickness of approximately 0.020 inch or less and is significantly shorter from where it exits the tailpipe 13 up to the tunnel to reduce the impact of the particulate sampler on the exhaust gas temperature. That is, utilizing a probe of a larger wall thickness, like that of the prior art, absorbs a greater amount of the thermal energy of the exhaust gas. As a result, dynamic testing is negatively impacted because the sample exhaust gas temperature will lag the actual exhaust gas temperature. Furthermore, the larger wall thickness lengthens static testing in that the sampler must be "warmed up" longer to reach the temperature of the exhaust gases.

Figure 3:
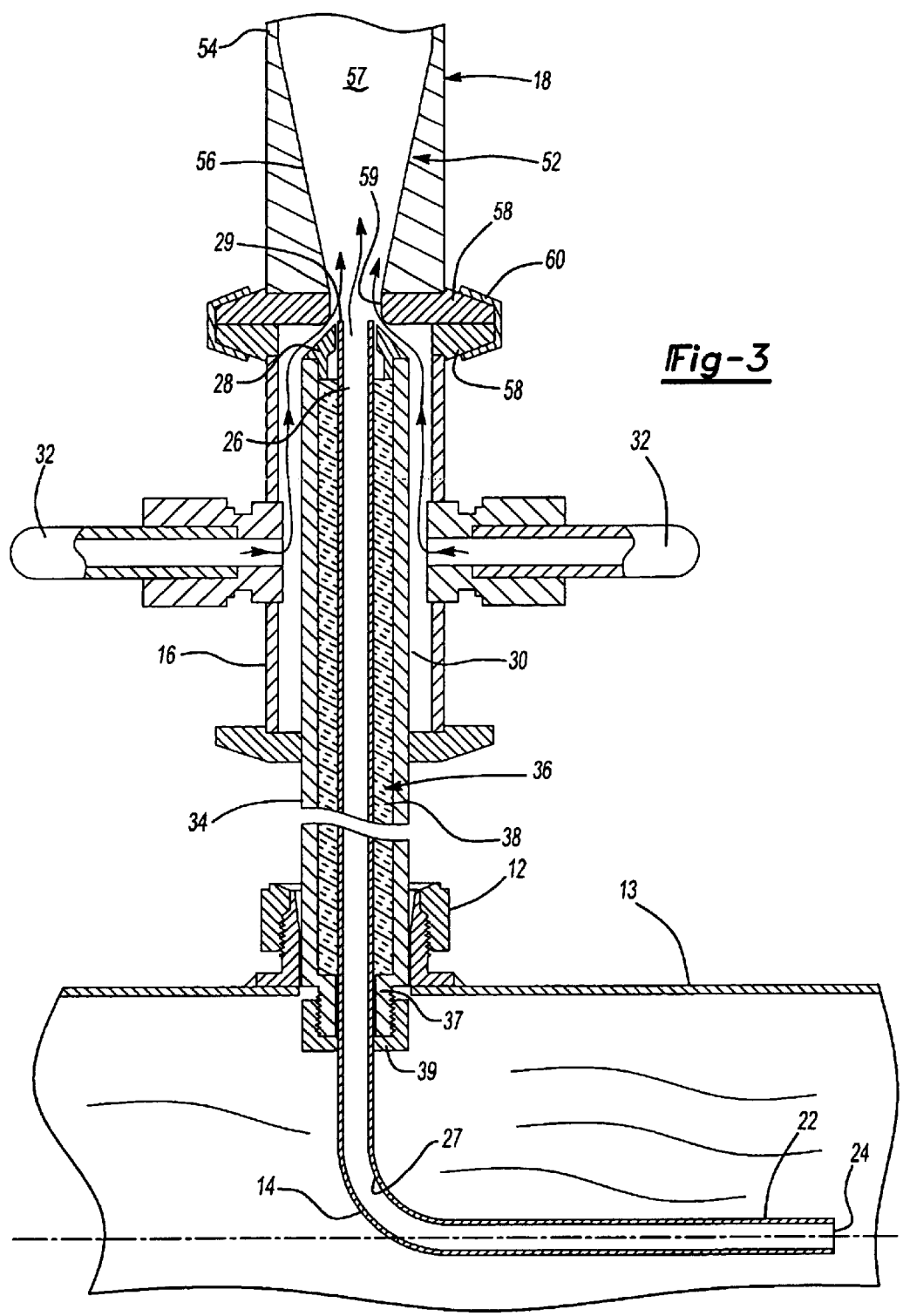
FIG. 3 is a cross-sectional view of one embodiment of the transfer tube assembly.

Utilizing a significantly shorter probe than the prior art may cause the sampler 10 to be more sensitive to pressure fluctuations present in the tail pipe. Cyclic pressure fluctuations are caused by internal combustion engines as the engine pistons reciprocate. During a pressure drop, sample exhaust gas and dilution gas may be undesirably drawn out of the probe and back into the tailpipe, thereby changing the dilution ratio in an uncontrolled manner. Referring to FIG. 3, the portion of the probe 14 within the tailpipe 13 may be lengthened to minimize the effects of the pressure fluctuations.

The transfer tube assembly of the present invention better maintains the temperature of the sample exhaust gas so that the impact of the sampler 10 and the ambient air on the temperature of the sample is reduced. With continuing reference to FIG. 3, the transfer tube assembly 12 includes an outer tube 34 surrounding the probe 14 to create an insulator cavity 36. The probe 14 is removable secured to an end 37 of the outer tube 34 by a threaded fastener 39 to permit disassembly of the transfer tube assembly 12 for cleaning. The insulator cavity 36 insulates the sample exhaust gas passageway 27 from the ambient air surrounding the transfer tube assembly 12 and the dilution gas in the dilution chamber 30 to maintain the temperature of the sample exhaust gas. Preferably, the probe 14 is insulated from the tail pipe to the tunnel 18 where the gases are homogenously mixed. Insulation 38 may be arranged in the insulator cavity 36, as shown in FIG. 3, or the air trapped in the insulator cavity 36 may simply be used. The end section 28 separates the outer tube 34 and the probe 14 to further insulate the sample exhaust gas until it is mixed with the dilution gas. To avoid cold spots on the probe 14 the end section 28 is spaced slightly from the outer circumference of the probe 14. The end section 28 may be constructed from ceramic material to provide enhanced insulation.

The diameter of the probe 14 is typically approximately 0.25 inch in diameter. The outer tube 34 may be approximately 0.75 inch in diameter or greater, but needs only be of a sufficient diameter to form a cavity around the probe 14 for insulation. As a result, one desirable ratio of the outer tube 34 to the probe 14 may be approximately 2:1 or 3:1, which provides a sufficiently large insulator cavity, however, it is to be understood that another ratio may be used depending on the amount of insulation and other parameters.

Figure 4:
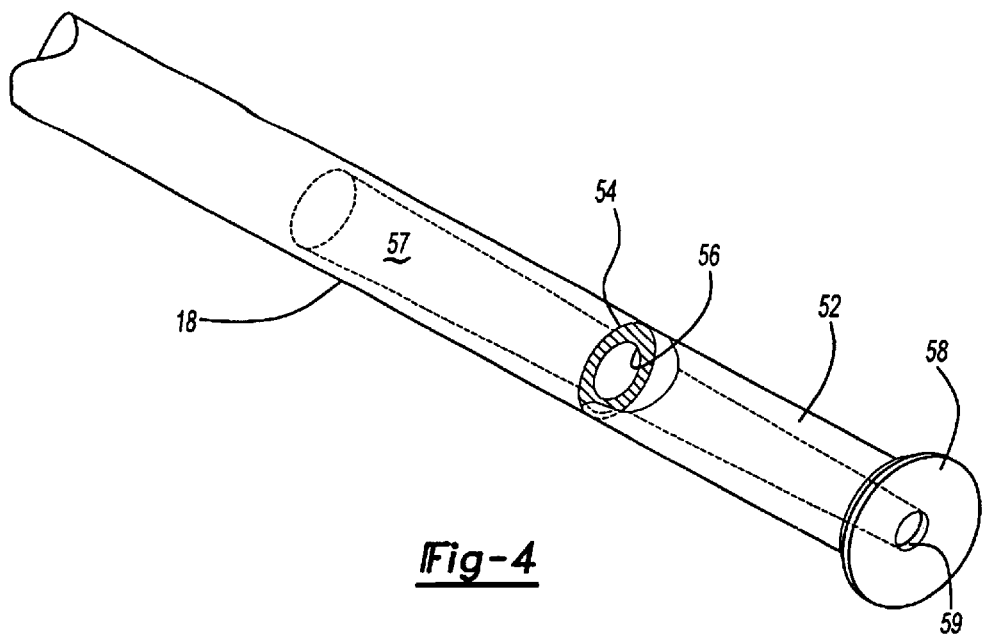
FIG. 4 is a partially broken-away perspective view of a tunnel of the present invention.

Prior art tunnels experience problems with particulate matter collecting on the interior passageways thereby negatively impacting the accuracy of the particulate matter measured. Specifically, prior art tunnels utilized long cylindrical tubes. The inner diameter of the tubes was larger than the inner diameter of the probe, which is connected to the tunnel. As a result, a recirculating flow area was created in which particulate matter would collect adjacent to the probe within the tunnel. The tunnel 18 of the present invention, as shown in detail in FIG. 4, includes a tapered end portion 52 adjacent to the mixer 16. The tunnel 18 preferably includes an outer tube 54, which is approximately 1.25 inch in outer diameter (1.125 inch in inner diameter) and 2½ feet in length. It should be understood that any other suitable diameter may be used.

An inner tube 56 is arranged coaxially with the outer tube 54 and defines a gas mixing passageway 57. The tapered end portion or diffusor 52, which has an angle of 8° to 12°, tapers towards the mixer 16 to form a frustoconical shape that prevents particulate matter from collecting in the gas mixing passageway 57. The tubes 54 and 56 are secured in any suitable manner. The opening in the diffuser 52, which has a diameter of 0.3 to 0.5 inch, forms the mixing orifice 59 and is aligned with the second end portion 26 of the probe. The tunnel 18 and the mixer 16 include flanges 58 that are secured to one another with a clamp 60. The flange 58 on the tunnel 18 comprises the mixing orifice 59 arranged between the second end portion 26 and the gas mixing passageway 57. The dilution and sample exhaust gases commingle prior to flowing through the orifice 59 and into the gas mixing passageway 57.

The exhaust gas is received by the probe 14 and the mixer 16 introduces dilution gas to the sample exhaust gas. As the sample exhaust gas flows through the probe 14, the effect of the probe on the temperature of sample exhaust gas is minimized by the reduced wall thickness. Furthermore, the sample exhaust gas temperature is maintained by the insulator cavity 36 as it flows through the transfer assembly 12. The dilution gas and exhaust gas flow into the tunnel 18 where they are homogeneously mixed together. The tunnel 18 tapers toward the transfer tube assembly 12 so that particulate matter does not accumulate in the tunnel 18. The exhaust gas sample may then be collected in a filter or sent to an analyzer for a more detailed analysis.

Figure 5:
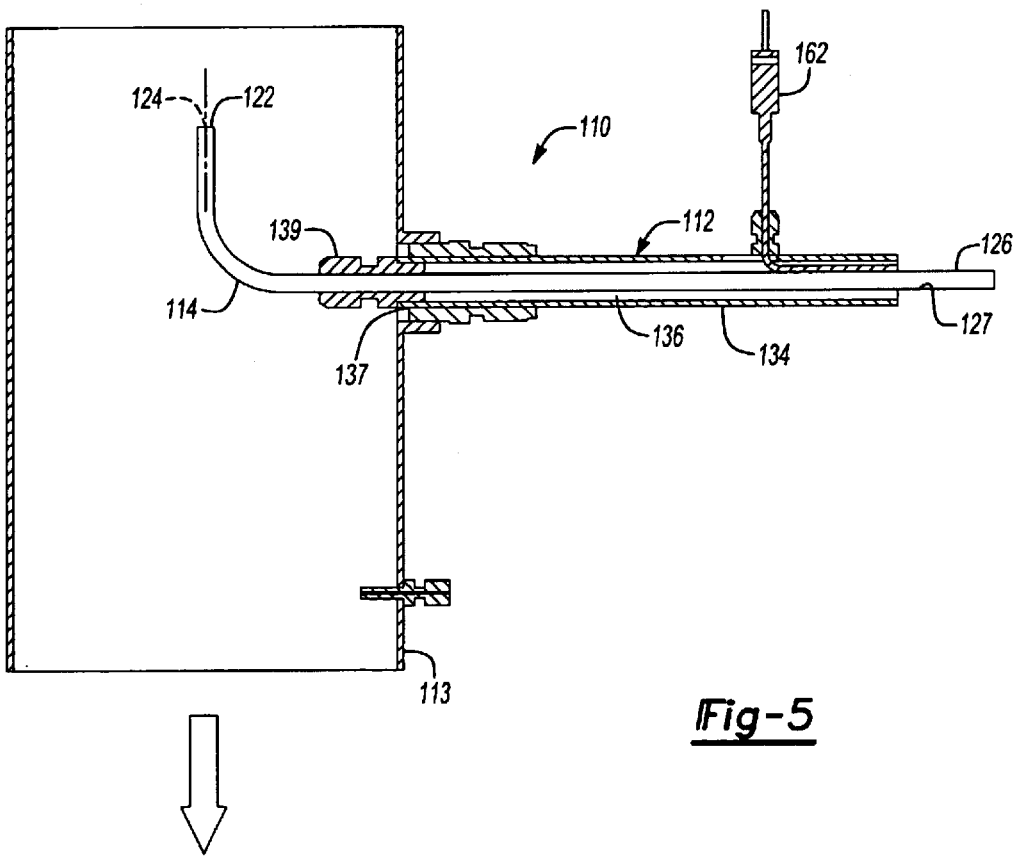
FIG. 5 is a cross-sectional view of a probe and transfer tube of another particulate sampler.

Another particulate sampler is shown in FIGS. 5–9 and functions similarly to the sampler 10 described above. Referring to FIG. 5, the sampler 110 includes a transfer tube assembly 112 supported on a tailpipe 113. The probe 114 includes a first end portion 122 with an opening 124 extending to a second end portion 126. The probe 114 defines a sample exhaust gas passageway 127 that carries exhaust gases from the tailpipe 113 to the mixer. The second end portion 126 extends beyond the outer tube 134. A fitting 139 at an end 139 of the outer tube 134 supports a portion of the probe 114. The outer tube 134 is spaced from the probe 114 to form an insulator cavity 136 around the probe 114 to insulate the sample exhaust gas until it is mixed with the dilution gas. A temperature sensor 162 may be used in close proximity to or in contact with the outer circumference of the probe 114 to monitor the temperature for determining whether the sample exhaust gas is being maintained at the desired temperature by the insulator cavity 136.

Figure 6:
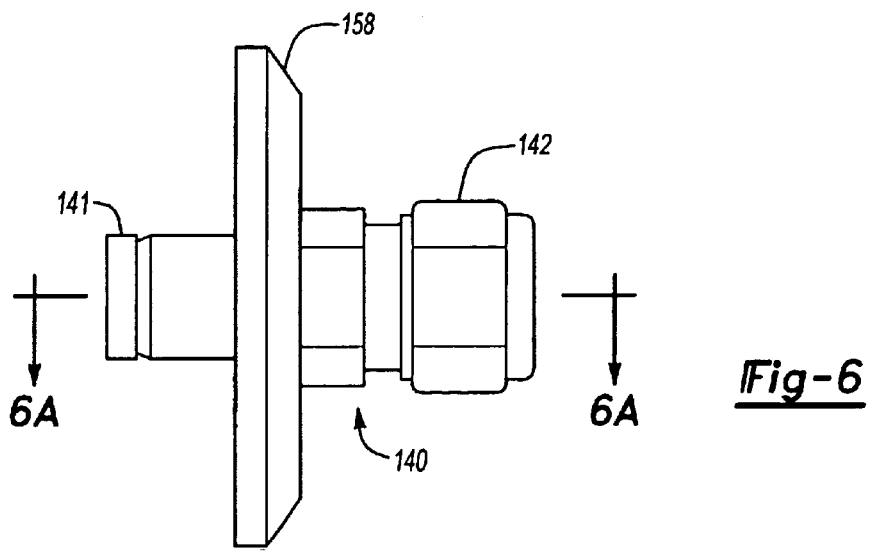
FIGS. 6 and 6A respectively are side and cross-sectional views of an end cap for receiving the probe and transfer tube shown in FIG. 5.
Figure 6A:
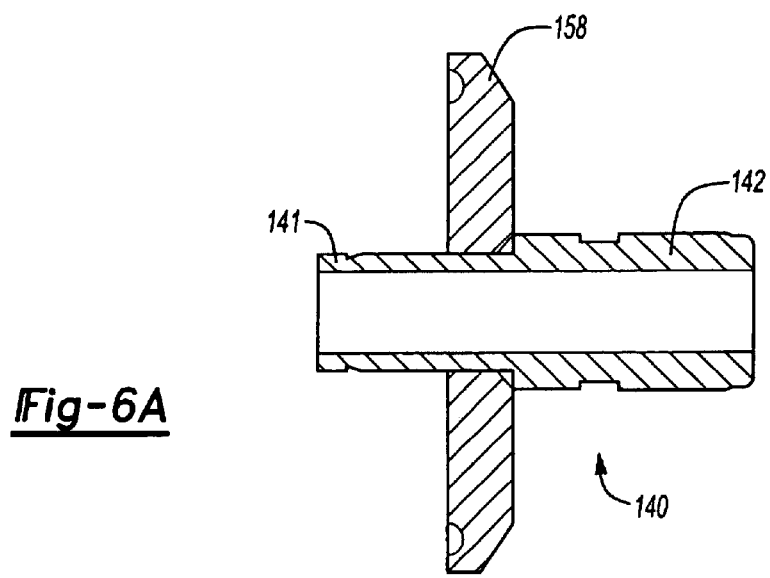
Figure 7:
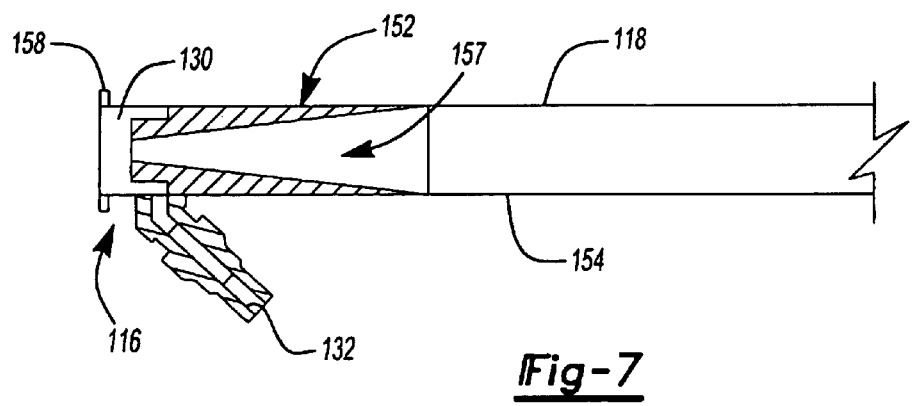
FIG. 7 is a cross-sectional view of a mixer and tunnel for securing to the end cap shown in FIGS. 6 and 6A.
Figure 8:
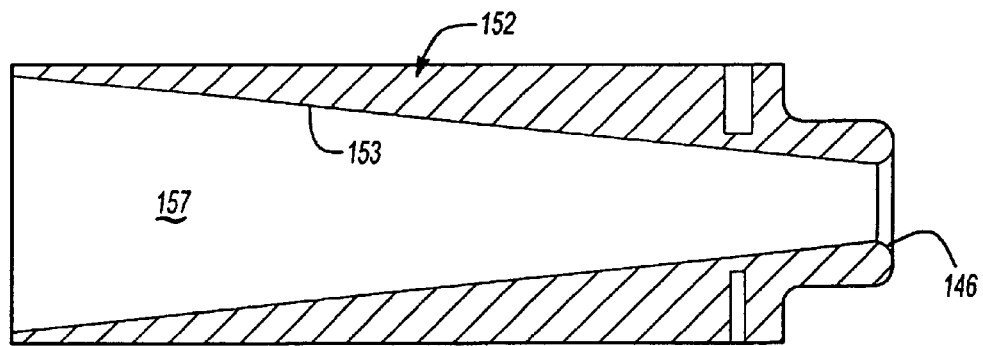
FIG. 8 is an enlarged cross-sectional view of the diffusor portion of the mixer.
Figure 9:
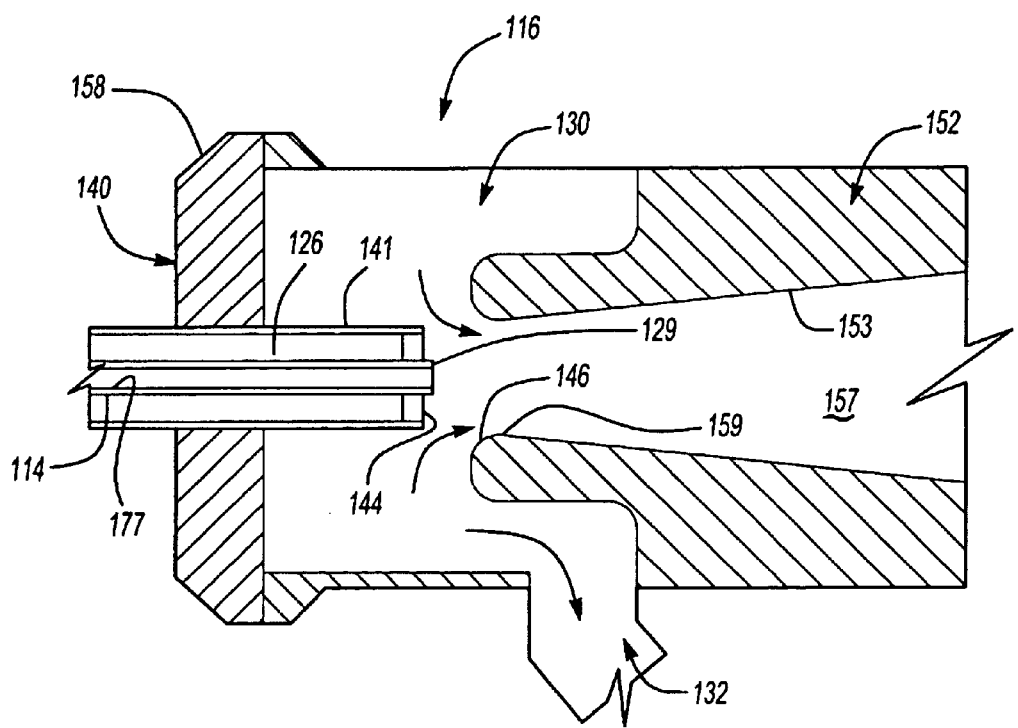
FIG. 9 is a cross-sectional view of the mixer.

Referring to FIGS. 6 and 6A, an end cap 142 receives the transfer tube assembly 112 and is secured to the mixer and tunnel, shown in FIG. 7, by a clamp at flanges 158. The second end 126 is disposed within the end cap 140; the end cap 140 includes a compression fitting secured about the outer tube 134. An end 141 of the cap 140 may include a spacer 144 arranged about the second end 126 of the probe 114 to ensure that the exhaust gas passageway 127 is aligned with the mixing gas passageway 157, best shown in FIG. 9.

The mixer 116 defines a dilution gas chamber 130 receiving dilution gas from a feed tube 132. The mixer 116 includes a diffusor portion having a frustoconical tapered surface 153 tapering toward the second end 126 (best shown in FIG. 9). The diffusor 152 may be secured to the tunnel 118 by welding or any other suitable means. The diffusor 152 defines the mixing orifice 159 and has a rounded leading edge, shown in FIG. 8, adjacent to the dilution gas chamber 130 and second end 126 to enhance the flow of the dilution and sample exhaust gases into the diffusor 152. The radius of the leading edge is relatively small such as approximately 0.075 inch.

The invention has been described in an illustrative manner, and it is to be understood that the terminology that has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

What is claimed is:

1. A particulate sampler for use in analyzing particulate matter in exhaust gas from an emissions source, said sampler comprising:

a transfer tube assembly including a probe at least partially defining a sample exhaust gas passageway having a first end portion with an opening for receiving the exhaust gas from the emissions source and extending to a second end portion, said transfer tube assembly includes an outer tube surrounding at least a portion of said probe to define an insulator cavity to maintain a temperature of the exhaust gas in said sample exhaust gas passageway, wherein said probe has a wall thickness of approximately 0.020 inch and less;

a mixer receiving said second end portion, said mixer including a dilution gas passageway for carrying a dilution gas with said dilution gas passageway in communication with said sample exhaust gas passageway for introducing dilution gas to the exhaust gas; and a tunnel connected to said mixer and including a gas mixing passageway extending a length for homogeneously mixing the gases together with a mixing orifice arranged between said second end portion and said gas mixing passageway, and the exhaust gas and the dilution gas commingling prior to flowing through said orifice to said gas mixing passageway.

2. A particulate sampler for use in analyzing particulate matter in exhaust gas from an emissions source, said sampler comprising:

a transfer tube assembly including a probe at least partially defining a sample exhaust gas passageway having a first end portion with an opening for receiving the exhaust gas from the emissions source and extending to a second end portion, said transfer tube assembly includes an outer tube surrounding at least a portion of said probe to define an insulator cavity to maintain a temperature of the exhaust gas in said sample exhaust gas passageway;

a mixer receiving said second end portion, said mixer including a dilution gas passageway for carrying a dilution gas with said dilution gas passageway in communication with said sample exhaust gas passageway for introducing dilution gas to the exhaust gas;

a tunnel connected to said mixer and including a gas mixing passageway extending a length for homogeneously mixing the gases together with a mixing orifice arranged between said second end portion and said gas mixing passageway, and the exhaust gas and the dilution gas commingling prior to flowing through said orifice to said gas mixing passageway, wherein said mixer includes a portion forming a dilution gas chamber, surrounding at least a portion of said outer tube, said dilution gas passageway defined by at least one feed tube for carrying a dilution gas to said dilution gas chamber; and first and second feed tubes spaced apart from one another transverse to said outer tube.

3. A particulate sampler for use in analyzing particulate matter in exhaust gas from an emissions source, said sampler comprising:

a transfer tube assembly including a probe at least partially defining a sample exhaust gas passageway having a first end portion with an opening for receiving the exhaust gas from the emissions source and extending to a second end portion, said transfer tube assembly includes an outer tube surrounding at least a portion of said probe to define an insulator cavity to maintain a temperature of the exhaust gas in said sample exhaust gas passageway;

a mixer receiving said second end portion, said mixer including a dilution gas passageway for carrying a dilution gas with said dilution gas passageway in communication with said sample exhaust gas passageway for introducing dilution gas to the exhaust gas;

a tunnel connected to said mixer and including a gas mixing passageway extending a length for homogeneously mixing the gases together with a mixing orifice arranged between said second end portion and said gas mixing passageway, and the exhaust gas and the dilution gas commingling prior to flowing through said orifice to said gas mixing passageway, wherein said mixer includes a portion forming a dilution gas chamber, surrounding at least a portion of said outer tube, said dilution gas passageway defined by at least one feed tube for carrying a dilution gas to said dilution gas chamber; and first and second feed tubes spaced apart from one another transverse to said outer tube, wherein said feed tubes are arranged generally opposite one another relative to the dilution gas chamber, and said feed tubes curved toward one another and joined by a common fluid connection.

4. A particulate sampler for use in analyzing particulate matter in exhaust gas from an emissions source, said sampler comprising:

a transfer tube assembly including a probe at least partially defining a sample exhaust gas passageway having a first end portion with an opening for receiving the exhaust gas from the emissions source and extending to a second end portion, said transfer tube assembly includes an outer tube surrounding at least a portion of said probe to define an insulator cavity to maintain a temperature of the exhaust gas in said sample exhaust gas passageway, wherein said probe has a wall thickness of approximately 0.020 inch and less; and a mixer receiving said second end portion and having a portion arranged concentrically thereabout forming a dilution gas chamber, said mixer including a dilution gas passageway arranged between said first and second end portions for carrying a dilution gas to said dilution gas chamber.

5. A particulate sampler for use in analyzing particulate matter in exhaust gas from an emissions source, said sampler comprising:

a transfer tube assembly including a probe at least partially defining a sample exhaust gas passageway having a first end portion with an opening for receiving the exhaust gas from the emissions source and extending to a second end portion, said transfer tube assembly includes an outer tube surrounding at least a portion of said probe to define an insulator cavity to maintain a temperature of the exhaust gas in said sample exhaust gas passageway; and a mixer receiving said second end portion and having a portion arranged concentrically thereabout forming a dilution gas chamber, said mixer including a dilution gas passageway arranged between said first and second end portions for carrying a dilution gas to said dilution gas chamber, wherein said mixer includes a portion forming a dilution gas chamber, surrounding at least a portion of said outer tube, said dilution gas passageway defined by at least one feed tube for carrying a dilution gas to said dilution gas chamber, including first and second feed tubes spaced apart from one another transverse to said outer tube.

6. A particulate sampler for use in analyzing particulate matter in exhaust gas from an emissions source, said sampler comprising:

a transfer tube assembly including a probe at least partially defining a sample exhaust gas passageway having a first end portion with an opening for receiving the exhaust gas from the emissions source and extending to a second end portion, said transfer tube assembly includes an outer tube surrounding at least a portion of said probe to define an insulator cavity to maintain a temperature of the exhaust gas in said sample exhaust gas passageway;

a mixer receiving said second end portion and having a portion arranged concentrically thereabout forming a dilution gas chamber, said mixer including a dilution gas passageway arranged between said first and second end portions for carrying a dilution gas to said dilution gas chamber, wherein said mixer includes a portion forming a dilution gas chamber, surrounding at least a portion of said outer tube, said dilution gas passageway defined by at least one feed tube for carrying a dilution gas to said dilution gas chamber; and first and second feed tubes spaced apart from one another transverse to said outer tube, wherein said feed tubes are arranged generally opposite one another relative to the dilution gas chamber, and said feed tubes curved toward one another and joined by a common fluid connection.

7. A particulate sampler for use in analyzing particulate matter in exhaust gas from an emissions source, said sampler comprising:

a transfer tube assembly including a probe having a wall thickness of approximately 0.020 inch and less and at least partially defining a sample exhaust gas passageway having a first end portion with an opening for receiving the exhaust gas from the emissions source and extending to a second end portion;

a mixer receiving said second end portion and forming a dilution gas chamber, said mixer including a dilution gas passageway for carrying a dilution gas to said dilution gas chamber; and wherein said transfer tube assembly includes an outer tube extending from a connection to said mixer with said outer tube surrounding at least a portion of said probe.

8. The sampler according to claim 7, wherein said probe is removably secured to an end of said outer tube at said connection by a threaded fastener for permitting disassembly of said transfer tube assembly for cleaning.

* * * * *